United States Patent
Collins et al.

(10) Patent No.: US 10,266,590 B2
(45) Date of Patent: Apr. 23, 2019

(54) METHODS RELATED TO BIOLOGICS

(71) Applicant: MOMENTA PHARMACEUTICALS, INC., Cambridge, MA (US)

(72) Inventors: Brian Edward Collins, Arlington, MA (US); Joseph Glajch, Nashua, NH (US); John Robblee, Concord, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/254,818

(22) Filed: Sep. 1, 2016

(65) Prior Publication Data

US 2017/0074890 A1   Mar. 16, 2017

Related U.S. Application Data

(60) Provisional application No. 62/214,441, filed on Sep. 4, 2015.

(51) Int. Cl.
*C07K 16/24* (2006.01)

(52) U.S. Cl.
CPC ........ *C07K 16/248* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 8,398,980 B2 | 3/2013 | Kano et al. | |
| 8,562,991 B2 | 10/2013 | Igawa et al. | |
| 8,734,800 B2 | 5/2014 | Kano et al. | |

OTHER PUBLICATIONS

Actemra® Prescribing Information dated Oct. 21, 2013, Genentech, Inc. (48 pages).
Anumula, KR., Advances in fluorescence derivatization methods for high-performance liquid chromatographic analysis of glycoprotein carbohydrates, Anal Biochem, 350(1):1-23 (2006).
Dick, LW Jr., et al., C-terminal lysine variants in fully human monoclonal antibodies: investigation of test methods and possible causes, Biotechnol Bioeng, 100(6):1132-43 (2008).
Hara, S. et al., Determination of Mono-O-acetylated N-Acetylneuraminic Acids in Human and Rat Sera by Fluorometric High-Performance Liquid Chromatography, Analytical Biochemistry, 179:162-166 (1989).
Hincal, Filiz, An Introduction to Safety Issues in Biosimilars/Follow-On Biopharmaceuticals, J Med CBR Def, 7:1-17 (2009).
Townsend, R., Analysis of Glycoconjugates Using High-pH Anion-Exchange Chromatography, Journal of Chromatography Library, 58:181-209 (1995).
Hossler, P. et al., Optimal and consistent protein glycosylation in mammalian cell culture, Glycobiology, 19(9):936.949 (2009).
Johnson, K. et al., Cation exchange-HPLC and mass spectrometry reveal C-terminal amidation of an IgG1 heavy chain, Analytical Biochemistry, 360:75-83 (2007).
Nowicki, Michal, Basic Facts about Biosimilars, Kidney & Blood Press Res. 30 267-272 (2007).
Schellekens, Huub, Biosimllar therapeutics—what do we need to consider?, NDT Plus, 2(Suppl 1):127-136 (2009).
Schiestl, M. et al., Acceptable changes in quality attributes of glycosylated biopharmaceuticals, Nature Biotechnology, 4:310-312 (2011).

*Primary Examiner* — Joseph Woitach
(74) *Attorney, Agent, or Firm* — Choate Hall & Stewart, LLP; Rolando Medina; Meaghan E. Bychowski

(57) ABSTRACT

The present invention relates to the characterization and production of biologics.

15 Claims, 1 Drawing Sheet
Specification includes a Sequence Listing.

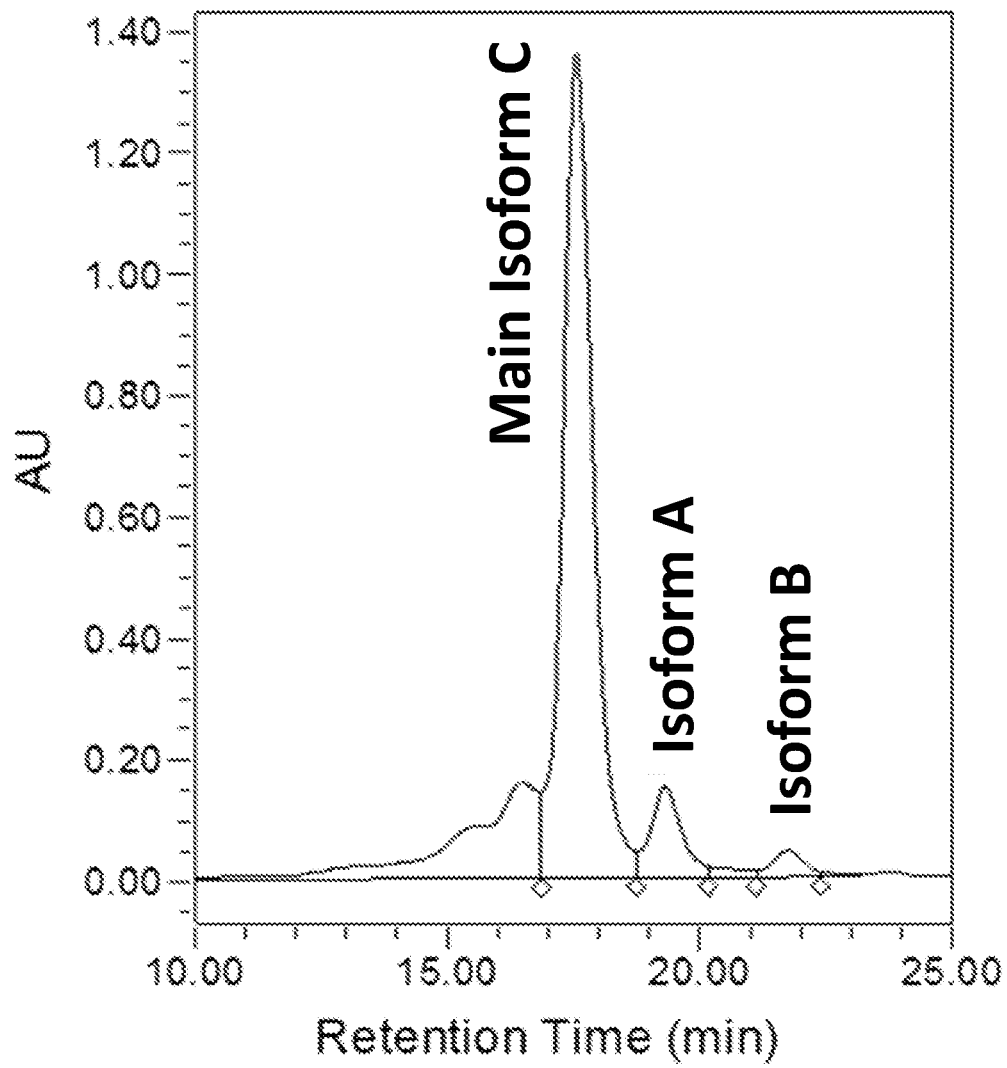

METHODS RELATED TO BIOLOGICS

CROSS REFERENCE TO RELATED APPLICATIONS

The present application claims the benefit of U.S. Provisional Application No. 62/214,441, filed on Sep. 4, 2015, the contents of which are herein incorporated by reference in their entirety.

SEQUENCE LISTING

In accordance with 37 CFR 1.52(e)(5), a Sequence Listing in the form of a text file (entitled "2010403-0070_SL.txt," created on Nov. 4, 2016, and 6.06 kilobytes in size) is incorporated herein by reference in its entirety.

BACKGROUND OF THE INVENTION

Tocilizumab (Actemra®) is a recombinant humanized monoclonal IgG1 antibody that binds to and inhibits the biologic activity of the interleukin-6 receptor (IL-6R) in in vitro and in vivo assay systems. Tocilizumab contains human framework regions and the complementarity-determining regions of a murine antibody that binds to IL-6R. Tocilizumab has an approximate molecular weight of 148 kD.

Tocilizumab is presently indicated for the treatment of (i) rheumatoid arthritis (RA): alone or in combination with methotrexate or one or more Disease-Modifying Anti-Rheumatic Drugs (DMARDs) in adult patients with moderately to severely active RA who have had an inadequate response to one or more DMARD (ii) polyarticular juvenile idiopathic arthritis (PJIA): alone or in combination with methotrexate in patients two years of age and older with active PJIA; and (iii) systemic juvenile idiopathic arthritis (SJIA): alone or in combination with methotrexate in patients two years of age and older with active SJIA (from Actemra® Prescribing Information dated Oct. 21, 2013, Genentech, Inc.).

For intravenous (IV) infusion Tocilizumab is supplied as a sterile, preservative-free solution with a pH of about 6.5 and a Tocilizumab concentration of 20 mg per mL. Single-use vials containing 80 mg per 4 mL, 200 mg per 10 mL, or 400 mg per 20 mL of tocilizumab are available for IV administration. Injectable solutions of tocilizumab are formulated in an aqueous solution containing disodium phosphate dodecahydrate and sodium dihydrogen phosphate dehydrate (as a 15 mmol per L phosphate buffer), polysorbate 80 (0.5 mg per mL), and sucrose (50 mg per mL). (from Actemra® Prescribing Information dated Oct. 21, 2013, Genentech, Inc.).

For subcutaneous administration tocilizumab is supplied as a sterile, colorless to yellowish, preservative-free liquid solution with an approximate pH 6.0. Tocilizumab is supplied as a 1 mL ready-to-use, single-use prefilled syringe (PFS) with a needle safety device. Each device delivers 0.9 mL (162 mg) of Tocilizumab, in a histidine buffered solution composed of tocilizumab (180 mg/mL), polysorbate 80, L-histidine and L-histidine monohydrochloride, L-arginine and L-arginine hydrochloride, L-methionine, and water for injection. (from Actemra® Prescribing Information dated Oct. 21, 2013, Genentech, Inc.).

SUMMARY OF THE INVENTION

The present disclosure provides, in part, methods of manufacturing a recombinant antibody drug product, comprising: providing or obtaining a test antibody preparation; determining (or acquiring a determination of) whether the level of antibody isoform A in the test antibody preparation is within a first pre-determined range, wherein antibody isoform A comprises a first amino acid sequence consisting of amino acids 1-214 of SEQ ID NO:1, a second amino acid sequence consisting of amino acids 1-448 of SEQ ID NO:2 and a third amino acid sequence consisting of amino acids 1-447 of SEQ ID NO:2 wherein amino acid 447 is a C-terminal Pro-$NH_2$, and/or determining (or acquiring a determination of) whether the level of antibody isoform B in the test antibody preparation is within a second pre-determined range, wherein antibody isoform B comprises a first amino acid sequence consisting of amino acids 1-214 of SEQ ID NO:1, a second amino acid sequence consisting of amino acids 1-447 of SEQ ID NO:2 wherein amino acid 447 is a C-terminal Pro-$NH_2$, and a third amino acid sequence consisting of amino acids 1-447 of SEQ ID NO:2 wherein amino acid 447 is a C-terminal Pro-$NH_2$; and processing at least a portion of the test antibody preparation as an antibody drug product if the level of antibody isoform A is within the first predetermined range and/or antibody isoform B is within the second predetermined range; thereby manufacturing an antibody drug product.

In some embodiments, the glutamine (Q) residue at the heavy chain N terminal of antibody isoform A is replaced with pyroglutamic acid. In some embodiments, the glutamine (Q) residue at the heavy chain N terminal of antibody isoform B is replaced with pyroglutamic acid.

In some embodiments, the level of antibody isoform A and/or the level of antibody isoform B is acquired for one, two, or more samples or batches of the test antibody preparation. In some embodiments, the level of antibody isoform A and/or the level of antibody isoform B is acquired for one, two, or more test antibody preparations.

In some embodiments, the method further comprises determining (or acquiring a determination of) whether the level of antibody isoform D in the test antibody preparation is within a first pre-determined range, wherein antibody isoform D comprises a first amino acid sequence consisting of amino acids 1-214 of SEQ ID NO:1, a second amino acid sequence consisting of amino acids 1-448 of SEQ ID NO:2, and a third amino acid sequence consisting of amino acids 1-447 of SEQ ID NO:2 and a C-terminal lysine.

In some embodiments, the method further comprises determining (or acquiring a determination of) whether the level of antibody isoform E in the test antibody preparation is within a first pre-determined range, wherein antibody isoform E comprises a first amino acid sequence consisting of amino acids 1-214 of SEQ ID NO:1, a second amino acid sequence consisting of amino acids 1-447 of SEQ ID NO:2 and a C-terminal lysine, and a third amino acid sequence consisting of amino acids 1-447 of SEQ ID NO:2 and a C-terminal lysine.

In some embodiments, the determining step comprises performing an analytical test on the test antibody preparation. In some embodiments, the processing step comprises combining the test antibody preparation with an excipient or buffer.

In some embodiments, the processing step comprises one or more of: formulating the test antibody preparation; processing the test antibody preparation into a drug product; combining the test antibody preparation with a second component, e.g., an excipient or buffer; changing the concentration of the test antibody in the preparation; lyophilizing the test antibody preparation; combining a first and second aliquot of the test antibody to provide a third, larger, aliquot; dividing the test antibody preparation into smaller aliquots; disposing the test antibody preparation into a container, e.g., a gas or liquid tight container; packaging the test antibody preparation; associating a container comprising the test antibody preparation with a label (e.g., labeling); shipping or moving the test antibody preparation to a different location.

In some embodiments, the processed drug product is approved under Section 351(k) of the Public Health Service (PHS) Act. In some embodiments, the processed drug product is not approved under biologics license application (BLA) under Section 351(a) of the Public Health Service (PHS) Act. In some embodiments, one or more, including all, of the reference criteria shown in Table 1 is/are a specification for commercial release of a drug product under Section 351(k) of the Public Health Service (PHS) Act.

The present disclosure provides, in part, methods of manufacturing a recombinant antibody drug product, comprising: providing or obtaining a test antibody preparation; determining (or acquiring a determination of) whether the level of antibody isoform A in the test antibody preparation is within a first pre-determined range, wherein antibody isoform A comprises a first amino acid sequence consisting of amino acids 1-214 of SEQ ID NO:1, a second amino acid sequence consisting of amino acids 1-448 of SEQ ID NO:2 and a third amino acid sequence consisting of amino acids 1-447 of SEQ ID NO:2 wherein amino acid 447 is a C-terminal Pro-NH$_2$, and processing at least a portion of the test antibody preparation as an antibody drug product if the level of antibody isoform A is within the first predetermined range, thereby manufacturing an antibody drug product.

In some embodiments, the glutamine (Q) residue at the heavy chain N terminal of antibody isoform A is replaced with pyroglutamic acid. In some embodiments, the glutamine (Q) residue at the heavy chain N terminal of antibody isoform B is replaced with pyroglutamic acid.

In some embodiments, the level of antibody isoform A and/or the level of antibody isoform B is acquired for one, two, or more samples or batches of the test antibody preparation. In some embodiments, the level of antibody isoform A and/or the level of antibody isoform B is acquired for one, two, or more test antibody preparations.

In some embodiments, the method further comprises determining (or acquiring a determination of) whether the level of antibody isoform D in the test antibody preparation is within a first pre-determined range, wherein antibody isoform D comprises a first amino acid sequence consisting of amino acids 1-214 of SEQ ID NO:1, a second amino acid sequence consisting of amino acids 1-448 of SEQ ID NO:2, and a third amino acid sequence consisting of amino acids 1-447 of SEQ ID NO:2 and a C-terminal lysine.

In some embodiments, the method further comprises determining (or acquiring a determination of) whether the level of antibody isoform E in the test antibody preparation is within a first pre-determined range, wherein antibody isoform E comprises a first amino acid sequence consisting of amino acids 1-214 of SEQ ID NO:1, a second amino acid sequence consisting of amino acids 1-447 of SEQ ID NO:2 and a C-terminal lysine, and a third amino acid sequence consisting of amino acids 1-447 of SEQ ID NO:2 and a C-terminal lysine.

In some embodiments, the determining step comprises performing an analytical test on the test antibody preparation. In some embodiments, the processing step comprises combining the test antibody preparation with an excipient or buffer.

In some embodiments, the processing step comprises one or more of: formulating the test antibody preparation; processing the test antibody preparation into a drug product; combining the test antibody preparation with a second component, e.g., an excipient or buffer; changing the concentration of the test antibody in the preparation; lyophilizing the test antibody preparation; combining a first and second aliquot of the test antibody to provide a third, larger, aliquot; dividing the test antibody preparation into smaller aliquots; disposing the test antibody preparation into a container, e.g., a gas or liquid tight container; packaging the test antibody preparation; associating a container comprising the test antibody preparation with a label (e.g., labeling); shipping or moving the test antibody preparation to a different location.

In some embodiments, the processed drug product is approved under Section 351(k) of the Public Health Service (PHS) Act. In some embodiments, the processed drug product is not approved under biologics license application (BLA) under Section 351(a) of the Public Health Service (PHS) Act. In some embodiments, one or more, including all, of the reference criteria shown in Table 1 is/are a specification for commercial release of a drug product under Section 351(k) of the Public Health Service (PHS) Act.

The present disclosure provides, in part, methods of manufacturing a recombinant antibody drug product, comprising: providing or obtaining a test antibody preparation; determining (or acquiring a determination of) whether the level of antibody isoform B in the test antibody preparation is within a second pre-determined range, wherein antibody isoform B comprises a first amino acid sequence consisting of amino acids 1-214 of SEQ ID NO:1, a second amino acid sequence consisting of amino acids 1-447 of SEQ ID NO:2 wherein amino acid 447 is a C-terminal Pro-NH$_2$, and a third amino acid sequence consisting of amino acids 1-447 of SEQ ID NO:2 wherein amino acid 447 is a C-terminal Pro-NH$_2$; and processing at least a portion of the test antibody preparation as an antibody drug product if the level of antibody isoform B is within the second predetermined range, thereby manufacturing an antibody drug product.

In some embodiments, the glutamine (Q) residue at the heavy chain N terminal of antibody isoform A is replaced with pyroglutamic acid. In some embodiments, the glutamine (Q) residue at the heavy chain N terminal of antibody isoform B is replaced with pyroglutamic acid.

In some embodiments, the level of antibody isoform A and/or the level of antibody isoform B is acquired for one, two, or more samples or batches of the test antibody preparation. In some embodiments, the level of antibody isoform A and/or the level of antibody isoform B is acquired for one, two, or more test antibody preparations.

In some embodiments, the method further comprises determining (or acquiring a determination of) whether the level of antibody isoform D in the test antibody preparation is within a first pre-determined range, wherein antibody isoform D comprises a first amino acid sequence consisting of amino acids 1-214 of SEQ ID NO:1, a second amino acid sequence consisting of amino acids 1-448 of SEQ ID NO:2, and a third amino acid sequence consisting of amino acids 1-447 of SEQ ID NO:2 and a C-terminal lysine.

In some embodiments, the method further comprises determining (or acquiring a determination of) whether the level of antibody isoform E in the test antibody preparation is within a first pre-determined range, wherein antibody isoform E comprises a first amino acid sequence consisting of amino acids 1-214 of SEQ ID NO:1, a second amino acid sequence consisting of amino acids 1-447 of SEQ ID NO:2 and a C-terminal lysine, and a third amino acid sequence consisting of amino acids 1-447 of SEQ ID NO:2 and a C-terminal lysine.

In some embodiments, the determining step comprises performing an analytical test on the test antibody preparation. In some embodiments, the processing step comprises combining the test antibody preparation with an excipient or buffer.

In some embodiments, the processing step comprises one or more of: formulating the test antibody preparation; processing the test antibody preparation into a drug product; combining the test antibody preparation with a second component, e.g., an excipient or buffer; changing the concentration of the test antibody in the preparation; lyophilizing the test antibody preparation; combining a first and second aliquot of the test antibody to provide a third, larger, aliquot; dividing the test antibody preparation into smaller aliquots; disposing the test antibody preparation into a container, e.g., a gas or liquid tight container; packaging the test antibody preparation; associating a container comprising the test antibody preparation with a label (e.g., labeling); shipping or moving the test antibody preparation to a different location.

In some embodiments, the processed drug product is approved under Section 351(k) of the Public Health Service (PHS) Act. In some embodiments, the processed drug product is not approved under biologics license application (BLA) under Section 351(a) of the Public Health Service (PHS) Act. In some embodiments, one or more, including all, of the reference criteria shown in Table 1 is/are a specification for commercial release of a drug product under Section 351(k) of the Public Health Service (PHS) Act.

Such information is also useful in monitoring product changes and controlling structural drift that may occur as a result of manufacturing changes. One exemplary report states that "[t]he size and complexity of . . . therapeutic proteins make the production of an exact replica almost impossible; therefore, there are no true generic forms of these proteins . . . . Verification of the similarity of biosimilars to innovator medicines remains a key challenge." (Hincal et al "An Introduction To Safety Issues In Biosimilars/Follow-On Biopharmaceuticals", J. Med. CBR Def, 7:1-18, (2009)). This disclosure provides, in part, methods and compositions sufficient to make and test products that qualify as tocilizumab, e.g., that are interchangeable versions of Actemra®.

Definitions

As used herein, a tocilizumab signature comprises a plurality of tocilizumab-specific parameters that define tocilizumab. In some instances, a tocilizumab signature can be a pharmaceutical specification, a commercial product release specification, a product acceptance criterion, a pharmacopeial standard, or a product labeling description. In some instances, the tocilizumab signature comprises a plurality of tocilizumab-specific parameters shown in Table 1:

TABLE 1

| Tocilizumab-Specific Parameters | | | |
|---|---|---|---|
| | Parameter | Sequence | |
| Parameter # | Category | Light Chain | Heavy Chain |
| 1 | Isoform A | 2 light chains consisting of amino acids 1-214 of SEQ ID NO: 1 | 1 heavy chain consisting of amino acids 1-447 of SEQ ID NO: 2 wherein amino acid 447 is a C terminal Pro-NH$_2$; and 1 heavy chain consisting of amino acids 1-448 of SEQ ID NO: 2 |
| 2 | Isoform B | 2 light chains consisting of amino acids 1-214 of SEQ ID NO: 1 | 2 heavy chains consisting of amino acids 1-447 of SEQ ID NO: 2 wherein amino acid 447 is a C terminal Pro-NH$_2$ |
| 3 | Isoform C | 2 light chains consisting of amino acids 1-214 of SEQ ID NO: 1 | 2 heavy chains consisting of amino acids 1-448 of SEQ ID NO: 2 |

BRIEF DESCRIPTION OF THE FIGURES

FIG. 1 is an HPLC trace of an exemplary Tocilizumab preparation, depicting main isoform C, minor isoform A, and minor isoform B.

DETAILED DESCRIPTION OF THE INVENTION

Detailed, high resolution, physiochemical and/or structural information about Actemra® (e.g., related to the presence of signature glycan species or quantitative analyses ascribing site-specificity for backbone modifications) can be used in the manufacture of products that qualify as tocilizumab, e.g., that are interchangeable versions of Actemra®.

An antibody preparation (e.g., such as a drug substance or a precursor thereof) included herein is or includes an antibody that has a first amino acid sequence with at least 95% identity to SEQ ID NO:1 and a second amino acid sequence with at least 95% identity to SEQ ID NO:2. In some instances, the first and/or second amino acid sequence(s) have at least 96%, 97%, 98%, 99%, or 100% identity to SEQ ID NO:1 and/or at least 96%, 97%, 98%, 99%, or 100% identity to SEQ ID NO:2. In some instances, the first and/or second amino acid sequence(s) has 100% identity to SEQ ID NO:1 and 100% identity to SEQ ID NO:2. In some instances, the first and/or second amino acid sequence(s) has 100% identity to SEQ ID NO:1 and 100% identity to SEQ ID NO:2 except the amino acid 448 is replaced with a Pro-NH$_2$ residue.

In some instances, an antibody preparation (e.g., such as a drug substance or a precursor thereof) can be a sample from a proposed or test batch of tocilizumab drug substance or drug product. As used herein, a batch of an antibody preparation refers to a single production run of the antibody. Evaluation of different batches thus means evaluation of different production runs or batches. As used herein sample(s) refer to separately procured samples. For example, evaluation of separate samples could mean evaluation of different commercially available containers or vials of the same batch or from different batches. As used herein, tocilizumab is the generic, compendial, nonproprietary, or official FDA name for the product marketed as Actemra® by Genentech/Roche Group and a product that is interchangeable with or equivalent to the product marketed as Actemra®.

As used herein, "determining" means evaluating, reviewing, considering, assessing, analyzing, measuring, and/or detecting the presence, absence, level, and/or ratio of one or more tocilizumab-specific parameters in an antibody preparation to provide information pertaining to the one or more tocilizumab-specific parameters. In some instances, determining can include performing a process that involves a physical change in a sample or another substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Determining can include performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent.

Information (e.g., value(s)) pertaining to a tocilizumab-specific parameter or a tocilizumab-specific parameter means information, regardless of form, that describes the presence, absence, abundance, absolute or relative amount, ratio (with another entity), or distribution of a tocilizumab-specific parameters. Information is evaluated in an antibody preparation as disclosed herein. Information is also conveyed in a tocilizumab signature. Information can be qualitative, e.g., present, absent, intermediate, or quantitative, e.g., a numerical value such as a single number, or a range, for a parameter. In some instances, information is from a single sample or batch or a plurality of samples or batches. In some instances, information can be a range or average (or other measure of central tendency), e.g., based on the values from any X samples or batches, e.g., wherein at least of the samples or batches is being evaluated for commercial release, wherein X is equal to, at least, or no more than, 2, 3, 4, 5, 6, 7, 8, 9, 10, 11, 12, 13, 14, 15, 16, or 17.

In some instances, information can be, for example: a statistical function, e.g., an average, of a number of values; a function of another value, e.g., of the presence, distribution or amount of a second entity present in the sample, e.g., an internal standard; a statistical function, e.g., an average, of a number of values; a function of another value, e.g., of the presence, distribution or amount of a second entity present in the sample, e.g., an internal standard; a value, e.g., a qualitative value, e.g., present, absent, "below limit of detection", "within normal limits" or intermediate. In some instances, information can be a quantitative value, e.g., a numerical value such as a single number, a range of values, a "no less than x amount" value, a "no more than x amount" value. In some instances, information can be abundance. Abundance can be expressed in relative terms, e.g., abundance can be expressed in terms of the abundance of a structure in relation to another component in the preparation. E.g., abundance can be expressed as: the abundance of an isoform in Table 1 relative to the amount of total antibody; the abundance of an isoform in Table 1 relative to the amount of a second isoform. Abundance, e.g., abundance of an isoform can be expressed as a relative proportion of the total antibody as, e.g., a proportion, ratio or percentage. Information can be expressed in any useful term or unit.

As used herein, acquire or acquiring (e.g., acquiring information) means obtaining possession of a physical entity, or a value, e.g., a numerical value, by "directly acquiring" or "indirectly acquiring" the physical entity or value. Directly acquiring means performing a process (e.g., performing an assay or test on a sample or "analyzing a sample" as that term is defined herein) to obtain the physical entity or value. Indirectly acquiring refers to receiving the physical entity or value from another party or source (e.g., a third party laboratory that directly acquired the physical entity or value). Directly acquiring a physical entity includes performing a process, e.g., analyzing a sample, that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent. Exemplary analytical methods are described herein.

As used herein "Section 351(k)" refers Section 351(k) of the Public Health Service (PHS) Act.

As used herein "Section 351(a)" refers to Section 351(a) the Public Health Service (PHS) Act.

All literature and similar material cited in this application, including, but not limited to, patents, patent applications, articles, books, treatises, and web pages, regardless of the format of such literature and similar materials, are expressly incorporated by reference in their entireties. In the event that one or more of the incorporated literature and similar materials differs from or contradicts this application, including but not limited to defined terms, term usage, described techniques, or the like, this application controls. The section headings used herein are for organizational purposes only and are not to be construed as limiting the subject matter described in any way.

These, and other aspects of the invention, are described in more detail below and in the claims.

Detailed, high resolution, physiochemical and/or structural information about Actemra® (e.g., related to the presence of signature isoforms can be used in the manufacture of products that qualify as tocilizumab, e.g., that are interchangeable versions of Actemra®). Such information is also useful in monitoring product changes and controlling sequence modifications that may occur as a result of manufacturing changes. One exemplary report states that "[t]he size and complexity of . . . therapeutic proteins make the production of an exact replica almost impossible; therefore, there are no true generic forms of these proteins . . . . Verification of the similarity of biosimilars to innovator medicines remains a key challenge." (Hincal "An Introduction To Safety Issues In Biosimilars/Follow-On Biopharmaceuticals", J. Med. CBR Def., 7:1-18, (2009).

This disclosure provides, in part, methods and compositions sufficient to make and test products that qualify as tocilizumab, e.g., that are interchangeable versions of Actemra®. In some instances, providing or obtaining an antibody preparation (e.g., such as an antibody drug substance or a precursor thereof), e.g., that is or includes an antibody, can include providing a host cell, e.g., a mammalian host cell (e.g., a CHO cell) that is genetically engineered to express an antibody having an amino acid sequence at least 95% identical to SEQ ID NO:1 and an amino acid sequence at least 95% identical to SEQ ID NO:2 (e.g., a genetically engineered cell); culturing the host cell under conditions suitable to express the glycoprotein (e.g., mRNA and/or protein); and, optionally, purifying the expressed glycoproteins, e.g., in the form of a recombinant antibody) from the cultured cell, thereby producing an antibody preparation. In some instances, the host cell is genetically engineered to express an antibody having an amino acid sequence at least 95%, 96%, 97%, 98%, 99%, or 100% identical to SEQ ID NO:1 and an amino acid sequence at least 95%, 96%, 97%, 98%, 99%, or 100% identical to SEQ ID NO:2, wherein the expressed amino acid sequences form a recombinant antibody composition. In some instances, the host cell is genetically engineered to express an antibody having an amino acid sequence is 100% identical to SEQ ID NO:1 and an amino acid sequence at least identical to SEQ ID NO:2, wherein the expressed amino acid sequences form a recombinant antibody composition. In some instances, the host cell is genetically engineered to express an antibody having an amino acid sequence is 100% identical to SEQ ID NO:1 and an amino acid sequence at least identical to SEQ ID NO:2 except the amino acid 448 is replaced with a Pro-NH$_2$ residue, wherein the expressed amino acid sequences form a recombinant antibody composition.

As used herein, percent (%) sequence identity with respect to a sequence is defined as the percentage of amino acid residues or nucleotides in a candidate sequence that are identical with the amino acid residues or nucleotides in the reference sequence, after aligning the sequences and introducing gaps, if necessary, to achieve the maximum percent sequence identity (e.g., gaps can be introduced in one or both of a first and a second amino acid or nucleic acid sequence for optimal alignment and non-homologous sequences can be disregarded for comparison purposes). Alignment for purposes of determining percent sequence identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximal alignment over the full length of the sequences being compared. In one embodiment, the length of a reference sequence aligned for comparison purposes is at least about 30%, e.g., at least about 40%, e.g., at least about 50%, at least about 60%, at least about 70%, at least about 80%, at least about 90%, or at least about 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. In some instances sequence identity refers to the amino acid sequence encoded by a nucleic acid that can be used to make the product.

In some instances, a tocilizumab signature disclosed herein can include 1, 2, or 3 of the tocilizumab specific parameters shown in Table 1 (e.g., including any combination of 1 or more (e.g., 2, or 3) of parameter numbers 1-3 shown in Table 1). In some instances, a tocilizumab signature disclosed herein can include, other structures or characteristics (whether intrinsic or extrinsic) of tocilizumab, e.g., that distinguish tocilizumab from non-tocilizumab glycoprotein (see application entitled Methods of Evaluating and Making Biologics, filed on Jun. 1, 2012, as U.S. Ser. No. 61/654,467, and application entitled Methods Related to Biologics, filed Sep. 4, 2015, as U.S. Ser. No. 62/214,419, for exemplary structures or characteristics). Examples of structures or characteristics include: the amount of GlNAc in the preparation (e.g., relative to total glycans of the preparation); the amount of truncated core glycans; the amount of aglycosylated glycans; the amount of each species of high mannose glycans; the amount of sialylated glycans or particular species of sialylated glycans; the ratio of monosialylated:diasylated glycans, the amount of diacetylated sialic acids (NeuXAc2), the amount of one or more of: NeuGc; NeuAc; Neu5,7,Ac2; Neu5Gc,9Ac; Neu5,8Ac2; Neu5,9Ac2; Neu4,5Ac2. Examples of parameters related to the glycan linkage composition of a glycoprotein preparation can be: the presence or amount of one or more of terminal fucose; terminal mannose; terminal galactose; 2 linked mannose; 3.6 linked mannose; terminal GlcNAc; terminal GalNAc; 4 linked GlcNAc; 4,6 linked GlcNAc. A parameter may also be the ratio of one of these to another or to another property. Examples of parameters related to the glycoform composition of a glycoprotein preparation include: the absence or presence of one or more specific glycoforms; the amount or abundance of a specific glycoform in the preparation relative to total glycoforms (e.g., in a w/w basis); the ratio of one particular glycoform to another. Examples of parameters related to post-translational modification in the preparation include: the absence or presence of one or more specific post-translational modification; the abundance or distribution of one or more specific post-translational modifications. In some instances, the present disclosure includes determining whether information evaluated for an antibody preparation meets a tocilizumab signature, e.g., by comparing the information with the tocilizumab signature and/or confirming that the information has a defined (e.g., predefined) relationship with the tocilizumab signature.

In some instances, methods disclosed herein can be used to confirm the identity and/or quality of tocilizumab preparations. For example, methods can include assessing preparations (e.g., samples, lots, and/or batches) of a test antibody to confirm whether the test antibody qualifies as tocilizumab, and, optionally, qualifying the test protein as tocilizumab if qualifying criteria (e.g. predefined qualifying criteria) are met; thereby evaluating, identifying, and/or producing (e.g., manufacturing) tocilizumab.

In some embodiments, the level of antibody isoform A and antibody isoform B of the preparation or sample of the preparation is expressed as a single value (e.g., an average value (or other value of central tendency plus or minus a window of variability (e.g., +/−0.5%, +/−1%, +/−5%, or +/−10%)) percentage of the total amount of protein (e.g., antibody) in the preparation or sample of the preparation; and the predetermined the level of antibody isoform A and antibody isoform B of the preparation or sample of the preparation of the validated sample is expressed as a range (e.g., a range including the minimum and maximum values of the range, and in some cases plus or minus a window of variability (e.g., +/−0.5%, +/−1%, +/−5%, or +/−10%)) percentage of the total amount of protein (e.g., antibody) in the validated sample. For example, in some instances a test antibody preparation or sample of a test antibody preparation qualifies (e.g., qualifies as tocilizumab, qualifies for use as tocilizumab, or qualifies for subsequent processing) as tocilizumab if the level of antibody isoform A and antibody isoform B of the preparation or sample of the preparation expressed as a single value (e.g., an average value (or other value of central tendency) plus or minus a window of variability (e.g., +/−0.5%, +/−1%, +/−5%, or +/−10%)) percentage of the total amount of protein (e.g., antibody) in the preparation or sample of the preparation falls within a predetermined range (e.g., a range including the minimum and maximum values of the range, and in some cases plus or minus a window of variability (e.g., +/−0.5%, +/−1%, +/−5%, or +/−10%)).

In some instances, a test antibody preparation or sample of a test antibody preparation qualifies (e.g., qualifies as tocilizumab, qualifies for use as tocilizumab, or qualifies for subsequent processing) if the level of antibody isoform A and antibody isoform B of the preparation or sample of the preparation assessed meets (e.g., corresponds with, satisfies, or falls within) a predetermined range (e.g., a range including the minimum and maximum values of the range, and in some cases plus or minus a window of variability (e.g., +/−0.5%, +/−1%, +/−5%, or +/−10%); or value (e.g., an average value (or other value of central tendency) plus or minus a window of variability (e.g., +/−0.5%, +/−1%, +/−5%, or +/−10%)). For example, a test antibody preparation or sample of a test antibody preparation qualifies as tocilizumab if the level of antibody isoform A and antibody isoform B of the preparation or sample of the preparation assessed corresponds to the level of isoform A and isoform B of a validated sample of tocilizumab. In some instances, the level of antibody isoform A and antibody isoform B of the preparation or sample of the preparation corresponds to the level of the validated sample if the level of the sample is within 80%-120% (e.g., 90%-110%, 95%-105%, 90%-100%, 95%-100%, 97%-110%) of the level of the isoform of the validated sample.

In some embodiments, the level of antibody isoform A and antibody isoform B of the preparation or sample of the preparation is expressed as a single value (e.g., an average value (or other value of central tendency) plus or minus a window of variability (e.g., +/−0.5%, +/−1%, +/−5%, or +/−10%)) and the predetermined the level of antibody isoform A and antibody isoform B of the preparation or sample of the preparation of the validated sample is also expressed as a single value (e.g., an average value (or other value of central tendency) plus or minus a window of variability (e.g., +/−0.5%, +/−1%, +/−5%, or +/−10%)). For example, in some instances a test antibody preparation or sample of a test antibody preparation qualifies (e.g., qualifies as tocilizumab, qualifies for use as tocilizumab, or qualifies for subsequent processing) as tocilizumab if the level of antibody isoform A and antibody isoform B of the preparation or sample of the preparation and expressed as a single value (e.g., an average value (or other value of central tendency) plus or minus a window of variability (e.g., +/−0.5%, +/−1%, +/−5%, or +/−10%)) falls within a certain percentage of (e.g., within 80%-120%) of the predetermined value.

In some embodiments, the level of antibody isoform A and antibody isoform B of the preparation or sample of the preparation is expressed as a single value (e.g., an average value (or other value of central tendency) plus or minus a window of variability (e.g., +/−0.5%, +/−1%, +/−5%, or +/−10%)) and the predetermined the level of antibody isoform A and antibody isoform B of the preparation or sample of the preparation of the validated sample is expressed as a range (e.g., a range including the minimum and maximum values of the range, and in some cases plus or minus a window of variability (e.g., +1-0.5%, +1-1%, +/−5%, or +/−10%)). For example, in some instances a test antibody preparation or sample of a test antibody preparation qualifies (e.g., qualifies as tocilizumab, qualifies for use as tocilizumab, or qualifies for subsequent processing) as tocilizumab if the level of antibody isoform A and antibody isoform B of the preparation or sample of the preparation and expressed as a single value (e.g., an average value (or other value of central tendency) plus or minus a window of variability (e.g., +/−0.5%, +/−1%, +/−5%, or +/−10%)) falls within a predetermined range (e.g., a range including the minimum and maximum values of the range, and in some cases plus or minus a window of variability (e.g., +/−0.5%, +/−1%, +/−5%, or +/−10%)).

In some instances, a test antibody preparation or sample of a test antibody preparation qualifies (e.g., qualifies as tocilizumab, qualifies for use as tocilizumab, or qualifies for subsequent processing) if the level of antibody isoform A and antibody isoform B of the preparation or sample of the preparation assessed falls within an acceptable range. In some instances, the acceptable range is expressed as a percentage of total amount of antibody in the preparation or sample of the preparation. For example, in some instances, the predetermined range of isoform A is 3%-15% (e.g., 3%-10%, 3%-9%, 4%-15%, 4%-10%, 4%-9%) of the total amount of antibody in the preparation or sample of the preparation. For example, in some instances, the predetermined range of isoform B is 0.5%-5% (e.g., 0.5%-4%, 0.5%-3%, 1%-5%, 1%-4%, 1%-3%, 1.5%-3%) of the total amount of antibody in the preparation or sample of the preparation.

The predetermined value or range as described herein and/or the value or range expressing the level of antibody isoform A and antibody isoform B can be recorded, e.g., using a recordable medium (e.g., on paper, in a computer readable medium, or in an ELN file, e.g., in a Certificate of Testing, Certificate of Analysis, Material Safety Data Sheet (MSDS), batch record, or Certificate of Analysis (CofA)).

Methods of the disclosure have a variety of applications and include, e.g., quality control at different stages of manufacture, analysis of tocilizumab preparations prior to or after completion of manufacture (e.g., prior to or after distribution to a fill/finish environment or facility), prior to or after release into commerce (e.g., before distribution to a pharmacy, a caregiver, a patient, or other end-user). Thus, the preparation can be any preparation that potentially comprises tocilizumab. In an embodiment the tocilizumab preparation is a drug substance (an active pharmaceutical ingredient or "API") or a drug product (an API formulated for use in a subject such as a human patient). In an embodiment the preparation is from a stage of manufacture or use that is prior to release to care givers or other end-users; prior to packaging into individual dosage forms, such as syringes, pens, vials, or multi-dose vials; prior to determination that the batch can be commercially released, prior to production of a Certificate of Testing, Material Safety Data Sheet (MSDS) or Certificate of Analysis (CofA) of the preparation. In an embodiment the glycoprotein preparation from an intermediate step in production, e.g., it is after secretion of the glycoprotein from a cell but prior to purification of drug substance.

Evaluations from methods of the invention are useful for guiding, controlling or implementing a number of activities or steps in the process of making, distributing, and monitoring and providing for the safe and efficacious use of tocilizumab. Thus, in an embodiment, e.g., responsive to the evaluation, e.g., depending on whether a criterion is met, a decision or step is taken. The method can further comprise one or both of the decision to take the step and/or carrying out the step itself. E.g., the step can comprise one in which the preparation (or another preparation for which the preparation is representative) is: classified; selected; accepted or discarded; released or processed into a drug product; rendered unusable for commercial release, e.g., by labeling it, sequestering it, or destroying it; passed on to a subsequent step in manufacture; reprocessed (e.g., the preparation may undergo a repetition of a previous process step or subjected to a corrective process); formulated, e.g., into drug substance or drug product; combined with another component, e.g., an excipient, buffer or diluent; disposed into a container; divided into smaller aliquots, e.g., unit doses, or multi-dose containers; combined with another preparation of tocilizumab; packaged; shipped; moved to a different location; combined with another element to form a kit; combined, e.g., placed into a package with a delivery device, diluent, or package insert; released into commerce; sold or offered for sale; delivered to a care giver or other end-user; or administered to a subject; e.g., based on the result of the determination or whether one or more subject entities is present, or upon comparison to a reference standard, the batch from which the preparation is taken can be processed, e.g., as just described.

Methods described herein may include making a decision: (a) as to whether a preparation may be formulated into drug substance or drug product; (b) as to whether a preparation may be reprocessed (e.g., the preparation may undergo a repetition of a previous process step); or (c) that the preparation is not suitable for formulation into drug substance or drug product. In instances the method comprises: formulating as referred to in step (a), reprocessing as referred to in step (b), or rendering the preparation unusable for commercial release, e.g., by labeling it or destroying it, as referred to in step (c).

Parameter Evaluation

The amino acid sequence of the main (most abundant) heavy chain sequence of tocilizumab (Actemra®) is disclosed herein as SEQ ID NO:2. The amino acid sequence of the light chain of tocilizumab (Actemra®) is disclosed herein as SEQ ID NO:1.

Tocilizumab LC Sequence:

SEQ ID NO: 1
DIQMTQSPSSLSASVGDRVTITCRASQDISSYLNWYQQKPGKAPKLLIY
YTSRLHSGVPSRFSGSGSGTDFTFTISSLQPEDIATYYCQQGNTLPYTF
GQGTKVEIKRTVAAPSVFIFPPSDEQLKSGTASVVCLLNNFYPREAKVQ
WKVDNALQSGNSQESVIEQDSKDSTYSLSSTLTLSKADYEKHKVYACEV
THQGLSSPVTKSFNRGEC

Tocilizumab Main Isoform HC Sequence:

SEQ ID NO: 2
EVQLQESGPGLVRPSQTLSLTCTVSGYSITSDHAWSWVRQPPGRGLEWI
GYISYSGITTYNPSLKSRVTMLRDTSKNQFSLRLSSVTAADTAVYYCAR
SLARTTAMDYWGQGSLVTVSSASTKGPSVFPLAPSSKSTSGGTAALGCL
VKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKG
QPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQK
SLSLSPG

Methods of Evaluation.

Parameters disclosed herein can be analyzed by any available suitable method. In some instances, isoform determination can be performed by ion exchange chromatography (Dick et al., Biotechnol. Bioeng., 100:1132-1143 (2008)) or LC-MS on either the intact or disulfide-reduced molecule (Dick et al., Biotechnol. Bioeng., 100:1132-1143 (2008)) or peptide LC-MS on C-terminal heavy chain peptides (Dick et al., Biotechnol. Bioeng., 100:1132-1143 (2008)).

In some instances, methods for evaluating one or more tocilizumab-specific parameters, e.g., in an antibody preparation, e.g., one or more of tocilizumab specific parameters disclosed in Table 1 in an antibody preparation are known in the art.

In some instances, techniques described herein may be combined with one or more other technologies for the detection, analysis, and or isolation of glycans or glycoproteins. For example, in certain instances, glycans are analyzed using one or more available methods (to give but a few examples, see Anumula, Anal. Biochem. 350(1):1, 2006; Klein et al., Anal. Biochem., 179:162, 1989; and/or Townsend, R. R. Carbohydrate Analysis" High Performance Liquid Chromatography and Capillary Electrophoresis., Ed. Z. El Rassi, pp 181-209, 1995, each of which is incorporated herein by reference in its entirety). For example, in some instances, glycans are characterized using one or more of chromatographic methods, electrophoretic methods, nuclear magnetic resonance methods, and combinations thereof.

Other Embodiments

This invention is further illustrated by the following examples which should not be construed as limiting. The contents of all references, patents and published patent applications cited throughout this application are incorporated herein by reference.

EXAMPLES

Example 1: Characterization of Tocilizumab

The therapeutic monoclonal antibody tocilizumab (trade name Actemra® in the US and RoActemra® in the EU) consists of two heavy chain and two light chain subunits held together by disulfide bonds. Tocilizumab samples were analyzed to determine the structural and sequence heterogeneity of the antibody samples.

As shown in FIG. 1, three antibody isoforms were found in each sample isoform A, isoform B, and isoform C (main isoform).

The main isoform (isoform C) contains two light chains consisting of the amino acid sequence set forth in SEQ ID NO:1, and two heavy chains consisting of amino acids 1-448 of the amino acid sequence set forth in SEQ ID NO:2. Minor isoform A contains two light chains consisting of the amino acid sequence set forth in SEQ ID NO:1, one heavy chain consisting of amino acids 1-448 of the amino acid sequence set forth in SEQ ID NO:2 and one heavy chain consisting of amino acids 1-447 of the amino acid sequence set forth in SEQ ID NO:2 wherein amino acid 447 is a C-terminal Pro-NH$_2$. Minor isoform B contains two light chains consisting of the amino acid sequence set forth in SEQ ID NO:1, and two heavy chains consisting of amino acids 1-447 of the amino acid sequence set forth in SEQ ID NO:2 amino acid 447 is a C-terminal Pro-NH$_2$. All heavy chain variants were detected at comparable levels in a separate LC-MS experiment in which heavy chain C-terminal peptides of disulfide-reduced samples were quantitated.

As shown in Table 2, the antibody samples contained different levels of minor isoform A and minor isoform B, with isoform A being more prevalent. Overall, the samples contained 4.7-8.2% minor isoform A (on average 6.5%) and between 1.7%-2.5% minor isoform B (on average 2.1%) (Table 2).

TABLE 2

Tocilizumab Characterization

| Sample | +Carboxypeptidase B | | |
|---|---|---|---|
| | Main Isoform C | Minor Isoform A | Minor Isoform B |
| Tocilizumab Sample A | 90% | 7.7% | 2.3% |
| Tocilizumab Sample B | 92.3% | 5.8% | 1.9% |
| Tocilizumab Sample C | 89.4% | 8.1% | 2.5% |
| Tocilizumab Sample D | 92.2% | 6.0% | 1.8% |
| Tocilizumab Sample E | 89.3% | 8.2% | 2.5% |
| Tocilizumab Sample F | 93.6% | 4.7% | 1.7% |
| Tocilizumab Sample G | 93.5% | 4.8% | 1.7% |
| Min | 89.3% | 4.7% | 1.7% |
| Max | 93.6% | 8.2% | 2.5% |
| Mean | 91.4% | 6.5% | 2.1% |

Example 2: Manufacture of Antibody Preparations

The determined percentage of antibody isoform A and isoform B described in Table 2 can be used to determine whether an antibody preparation qualifies for manufacturing into a tocilizumab drug product. For example, using tocilizumab antibody Sample A as an example, the level of main isoform A and/or main isoform B, e.g., in this case determined to be 7.7% and 2.3%, of the antibody sample. If the level of antibody isoform A and/or B falls within a certain predetermined range, the sample qualifies as tocilizumab and is processed as tocilizumab drug product. In this case, the specified range of isoform A is ~4.7%-8.2%; and the predetermined range of isoform B is ~1.7%-2.5%. Tocilizumab sample A, having a percentage of isoform A and isoform B of 7.7% and 2.3%, respectively, would therefore qualify as tocilizumab and be processed into tocilizumab drug product, e.g., combining the test antibody preparation with an excipient or buffer.

What is claimed is:

1. A method of manufacturing an antibody drug product, comprising:

acquiring a determination of whether the level of an antibody isoform A in a test antibody preparation is within a first pre-determined range of 3% to 15% of the total amount of antibody in the test antibody preparation, wherein the antibody isoform A comprises a light chain having at least 99% identity to SEQ ID NO:1, a first heavy chain having at least 99% identity to SEQ ID NO:2 and a second heavy chain having at least 99% identity to SEQ ID NO:2 wherein amino acid 447 is a C-terminal Pro-NH$_2$; or acquiring a determination of whether the level of an antibody isoform B in the test antibody preparation is within a second pre-determined range of 0.5% to 5% of the total amount of antibody in the test antibody preparation, wherein the antibody isoform B comprises a light chain having at least 99% identity to SEQ ID NO:1, a first heavy chain having at least 99% identity to SEQ ID NO:2 wherein amino acid 447 is a C-terminal Pro-NH$_2$, and a second heavy chain having at least 99% identity to SEQ ID NO:2 wherein amino acid 447 is a C-terminal Pro-NH$_2$; and processing at least a portion of the test antibody preparation as an antibody drug product if the level of the antibody isoform A is within the first predetermined range, the level of the antibody isoform B is within the second predetermined range, or both, thereby manufacturing the antibody drug product; or discarding at least a portion of the test antibody preparation if the level of the antibody isoform A is not within the first predetermined range, the level of the antibody isoform B is not within the second predetermined range, or both.

2. The method of claim 1, wherein the first predetermined range of the antibody isoform A is 4%-9% of the total amount of antibody in the test antibody preparation.

3. The method of claim 1, wherein the second predetermined range of the antibody iso form B is 1.5%-3% of the total amount of antibody in the test antibody preparation.

4. The method of claim 1, wherein the first amino acid residue of the first heavy chain of antibody isoform A, of the second heavy chain N of antibody isoform A, or of both, is pyroglutamic acid.

5. The method of claim 1, wherein the first amino acid residue of the first heavy chain of antibody isoform B, of the second heavy chain of antibody isoform B, or of both, is pyroglutamic acid.

6. The method of claim 1, wherein the method further comprises acquiring a determination of whether the level of an antibody isoform D in the test antibody preparation is within a third pre-determined range, wherein the antibody isoform D comprises a light chain having at least 99% identity to SEQ ID NO:1, a first heavy chain having at least 99% identity to SEQ ID NO:2, and a second heavy chain having at least 99% identity to SEQ ID NO:2 and comprising a C-terminal lysine.

7. The method of claim 1, wherein the method further comprises acquiring a determination of whether the level of an antibody isoform E in the test antibody preparation is within a fourth first pre-determined range, wherein the antibody isoform E comprises a light chain having at least 99% identity to SEQ ID NO:1, a first heavy chain having at least 99% identity to SEQ ID NO:2 and comprising a C-terminal lysine, and a second heavy chain having at least 99% identity to SEQ ID NO:2 and comprising a C-terminal lysine.

8. The method or claim 1, wherein the level of antibody isoform A, the level of antibody isoform B, or both is acquired for at least one sample of the test antibody preparation.

9. The method of claim 8, wherein the level or antibody isoform A, the level of antibody isoform B, or both is acquired for at least one sample of each of at least two batches of test antibody preparations.

10. The method of claim 1, wherein the acquiring step comprises performing an analytical test on the test antibody preparation.

11. The method of claim 1, wherein the processing step comprises combining at least a portion of the test antibody preparation with an excipient or buffer.

12. The method of claim 1, wherein the processing step comprises one or more of:
   formulating at least a portion of the test antibody preparation;
   combining al least a portion of the test antibody preparation with a second component;
   changing the concentration of the test antibody in at least a portion of the test antibody preparation;
   lyophilizing at least a portion of the test antibody preparation;
   combining a first and second aliquot of the test antibody preparation to provide a third, larger, aliquot;
   dividing at least a portion of the test antibody preparation into smaller aliquots;
   disposing at least a portion of the test antibody preparation into a container;
   packaging at least a portion of the test antibody preparation;
   associating a container comprising at least a portion of the test antibody preparation with a label; and
   shipping or moving at least a portion of the test antibody preparation to a different location.

13. The method of claim 1, wherein the antibody processed drug product is approval under Section 351(k) of the Public Health Service (PHS) Act.

14. The method of claim 1, wherein the antibody drug product is not approved under a biologics license application (BLA) under Section 351(a) of the Public Health Service (PHS) Act.

15. The method of claim 1, wherein one or more of the reference criteria shown in Table 1 is a specification for commercial release of the antibody drug product under Section 351(k) of the Public Health Service (PHS) Act.

* * * * *

```
                        SEQUENCE LISTING

<160> NUMBER OF SEQ ID NOS: 2

<210> SEQ ID NO 1
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
```

```
                    100                 105                 110
Pro Ser Val Phe Ile Phe Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 2
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240
```

-continued

```
Ser Val Phe Leu Phe Pro Pro Lys Pro Lys Asp Thr Leu Met Ile Ser
            245             250             255

Arg Thr Pro Glu Val Thr Cys Val Val Val Asp Val Ser His Glu Asp
            260             265             270

Pro Glu Val Lys Phe Asn Trp Tyr Val Asp Gly Val Glu Val His Asn
            275             280             285

Ala Lys Thr Lys Pro Arg Glu Glu Gln Tyr Asn Ser Thr Tyr Arg Val
    290             295             300

Val Ser Val Leu Thr Val Leu His Gln Asp Trp Leu Asn Gly Lys Glu
305             310             315             320

Tyr Lys Cys Lys Val Ser Asn Lys Ala Leu Pro Ala Pro Ile Glu Lys
            325             330             335

Thr Ile Ser Lys Ala Lys Gly Gln Pro Arg Glu Pro Gln Val Tyr Thr
            340             345             350

Leu Pro Pro Ser Arg Asp Glu Leu Thr Lys Asn Gln Val Ser Leu Thr
            355             360             365

Cys Leu Val Lys Gly Phe Tyr Pro Ser Asp Ile Ala Val Glu Trp Glu
    370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
            405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro Gly
    435             440             445
```